(12) United States Patent
Heilmann et al.

(10) Patent No.: US 12,728,082 B2
(45) Date of Patent: Sep. 8, 2026

(54) AQUEOUS OXIDATIVE COMPOSITION COMPRISING XANTHINE DERIVATIVES

(71) Applicant: Kao Corporation, Tokyo (JP)

(72) Inventors: Jens Heilmann, Darmstadt (DE); Diana Bauer, Darmstadt (DE); Steven Breakspear, Darmstadt (DE); Peter Bauer, Darmstadt (DE)

(73) Assignee: Kao Corporation, Tokyo (JP)

( * ) Notice: Subject to any disclaimer, the term of this patent is extended or adjusted under 35 U.S.C. 154(b) by 938 days.

(21) Appl. No.: 17/773,517

(22) PCT Filed: Oct. 30, 2020

(86) PCT No.: PCT/EP2020/080537

§ 371 (c)(1),
(2) Date: Apr. 29, 2022

(87) PCT Pub. No.: WO2021/084083

PCT Pub. Date: May 6, 2021

(65) Prior Publication Data

US 2022/0370314 A1 Nov. 24, 2022

(30) Foreign Application Priority Data

Oct. 31, 2019 (EP) .................................... 19206511

(51) Int. Cl.

| | |
|---|---|
| ***A61K 8/22*** | (2006.01) |
| ***A61G 5/04*** | (2013.01) |
| ***A61K 8/49*** | (2006.01) |
| ***A61Q 5/04*** | (2006.01) |
| ***A61Q 5/08*** | (2006.01) |
| ***A61Q 5/10*** | (2006.01) |

(52) U.S. Cl.

CPC .................. *A61K 8/22* (2013.01); *A61G 5/04* (2013.01); *A61K 8/4953* (2013.01); *A61Q 5/08* (2013.01); *A61Q 5/10* (2013.01); *A61K 2800/4324* (2013.01); *A61K 2800/882* (2013.01)

(58) Field of Classification Search

CPC ... A61K 8/22; A61Q 5/04; A61Q 5/08; A61Q 5/10

See application file for complete search history.

(56) References Cited

U.S. PATENT DOCUMENTS

| | | | | |
|---|---|---|---|---|
| 5,256,316 A * | 10/1993 | Suzuki | ...................... | C23F 3/06 252/79.3 |
| 2010/0158844 A1 | 6/2010 | Braida-Valerio et al. | | |
| 2015/0238398 A1 * | 8/2015 | Schafer | .................... | A61K 8/22 424/70.4 |
| 2018/0235857 A1 | 8/2018 | Pressly et al. | | |

FOREIGN PATENT DOCUMENTS

| | | | | |
|---|---|---|---|---|
| CN | 1411361 A | 4/2003 | | |
| DE | 10 2006 061 830 A1 | 6/2008 | | |
| DE | 10 2007 060 323 A1 | 1/2009 | | |
| DE | 10 2007 060 534 A1 | 1/2009 | | |
| DE | 10 2007 041 493 A1 | 3/2009 | | |
| EP | 1 221 932 A1 | 7/2002 | | |
| EP | 2 191 812 A1 | 6/2010 | | |
| EP | 2 198 923 A2 | 6/2010 | | |
| EP | 2 559 456 A2 | 2/2013 | | |
| JP | 2017115245 A * | 6/2017 | ................ | C23F 1/18 |
| WO | WO 01/28508 A1 | 4/2001 | | |
| WO | WO 2008/077688 A1 | 7/2008 | | |
| WO | WO 2009/030516 A2 | 3/2009 | | |
| WO | WO 2009/053180 A1 | 4/2009 | | |

OTHER PUBLICATIONS 1 molar HF, 2 molar H2O2, aqion—Online pH Calculator, 2025 (Year: 2025).*
DE 102007060534 A1 English machine translation (Year: 2009).*
International Search Report and Written Opinion issued Feb. 5, 2021 in PCT/EP2020/080537, filed on Oct. 30, 2020, 8 pages.
Extended European Search Report issued Apr. 9, 2020 in European Application 19206511.8, filed on Oct. 31, 2019, 5 pages.
Mintel #6713099, http://www.gnpd.com, 2 pages , 2019.

* cited by examiner

*Primary Examiner* — Susan T Tran
*Assistant Examiner* — William Craigo
(74) *Attorney, Agent, or Firm* — Oblon, McClelland, Maier & Neustadt, L.L.P.

(57) ABSTRACT

An aqueous oxidizing composition comprising a xanthine derivative is described. The composition may comprise more than 5% by weight of hydrogen peroxide. The composition may further comprise a lipophilic compound or a surfactant, and may be applied to keratin fibers. It has been unexpectedly found out that xanthine derivatives stabilize hydrogen peroxide compositions during storage.

10 Claims, No Drawings

AQUEOUS OXIDATIVE COMPOSITION COMPRISING XANTHINE DERIVATIVES

CROSS-REFERENCE TO RELATED APPLICATIONS

The present application is a 35 U.S.C. § 371 national stage application of International patent application PCT/EP2020/080537, filed Oct. 30, 2020, which is based on and claims the benefit of priority to European Application No. 19206511.8, filed Oct. 31, 2019. The entire contents of these applications are incorporated herein by reference.

FIELD OF THE INVENTION

The present invention relates to an aqueous oxidative composition comprising more than 5% by weight of hydrogen peroxide and certain xanthine derivatives. Furthermore, oxidative dyeing, bleaching, and perming processes using the composition are disclosed.

BACKGROUND OF THE INVENTION

Aqueous, hydrogen peroxide-containing compositions are well known in the art. These compositions are essential components in many industrial and artisanal processes. For example, bleaching or dyeing of solid substrates require the presence of oxidizing compositions. In particular paper, wool, and cosmetic industry rely on the performance of these compositions.

However, a common problem of such compositions is that the hydrogen peroxide tends to undergo a decomposition process during storage whereby the available active oxygen in the composition decreases over time. This decomposition process particularly represents a problem for bleaching, dyeing, and permanent waving processes. It is essential for the user of hydrogen-peroxide compositions that they have a long shelf life in order to retain their original performance.

The self-decomposition process of hydrogen peroxide increases with temperature. Thus, decomposition progresses faster in warm climate countries or under less than ideal storage conditions at the user's facilities. As a result, the user is confronted with lower performance in coloring, bleaching, or permanent waving processes compared to results obtained a couple of months ago with compositions having shorter storage times.

The prior art has not sufficiently solved this problem.

For example, EP2198923 focuses on formulation stability, but not on chemical stability of aqueous oxidizing composition.

Xanthine and its derivatives are well-known ingredients in pharmaceutical and food industry. Moreover, cleansing compositions comprising caffeine are well-known (e.g. Mintel #6713099).

WO2009/053180 discloses aqueous oxidizing compositions comprising 5% by weight or less of hydrogen peroxide and purine derivatives, in particular caffeine. It was found that purine derivatives reduce damage to keratin fibers.

SUMMARY OF THE INVENTION

The first object of the present invention is an aqueous oxidizing composition having a pH in the range of 1 to 6 comprising:

a) hydrogen peroxide at a concentration of more than 5% by weight, calculated to the total weight of the composition, and b) one or more compound(s) according to the following structure:

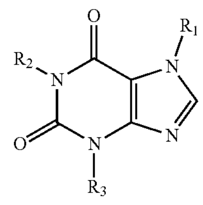

wherein $R_1$, $R_2$, and $R_3$ are independently selected from H and $CH_3$, and/or their mixtures.

The second object of the present invention is a method for stabilizing an aqueous oxidizing composition comprising the steps of:

i) providing an aqueous composition comprising hydrogen peroxide at a concentration of more than 5% by weight, calculated to the total of the composition, ii) dissolving in the composition as defined in step i) one or more compound(s) according to the following structure:

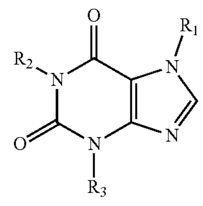

wherein $R_1$, $R_2$, and $R_3$ are independently selected from H and $CH_3$, and/or their mixtures.

The third object of the present invention is a method for oxidative dyeing of keratin fibers, preferably human keratin fibers, more preferably human hair, comprising the steps of:

iii) providing a composition as defined above, iv) mixing the composition with an aqueous composition having a pH in the range of 7 to 12 and comprising one or more oxidative dye precursors to prepare a ready-to-use composition having a pH in the range of 7 to 12, v) applying the ready-to-use composition onto keratin fibers and leaving it for a time period of 1 to 60 min, vi) rinsing off the keratin fibers and optionally shampooing the keratin fibers.

The fourth object of the present invention is a method for bleaching and/or lightening of keratin fibers, preferably human keratin fibers, more preferably human hair comprising the steps of:

vii) providing a composition as defined above, viii) mixing the composition with a bleach powder composition comprising one or more persalt(s) and/or peroxy salt(s) and one or more alkalizing agent(s) to prepare a ready-to-use composition having a pH in the range of 7 to 12, ix) applying the ready-to-use composition onto keratin fibers and leaving it for a time period in the range of 1 to 60 min, x) rinsing off the keratin fibers and optionally shampooing the keratin fibers.

The fifth object of the present invention is a method for bleaching and/or lightening of keratin fibers, preferably human keratin fibers, more preferably human hair comprising the steps of:

xi) providing a composition as defined above, xii) mixing the composition with an aqueous lightening composition comprising one or more one or more alkalizing agent(s) to prepare a ready-to-use composition having a pH in the range of 7 to 12, xiii) applying the ready-to-use composition onto keratin fibers and leaving it for a time period in the range of 1 to 60 min, xiv) rinsing off the keratin fibers and optionally shampooing the keratin fibers.

The sixth object of the present invention is a method for permanently shaping keratin fibers, preferably human keratin fibers, more preferably human hair, comprising the steps of:

xv) optionally shampooing the keratin fibers, xvi) putting hair under mechanical tension, xvii) applying to keratin fibers an aqueous composition having a pH in the range of 3 to 12 comprising one or more reducing agent(s) and one or more alkalizing agent(s), and leaving the composition for a time period in the range of 1 min to 60 min, xviii) optionally rinsing off the composition, xix) providing a composition as defined above, applying it to keratin fibers and leaving it for a time period in the range of 1 min to 30 min, xx) releasing mechanical tension from keratin fibers, xxi) rinsing off the keratin fibers and optionally shampooing the keratin fibers, with the provision that steps xvi) and xvii) as well as steps xix) and xx) may be performed in any order.

The seventh object of the present invention is a use of a compound according to the following general structure:

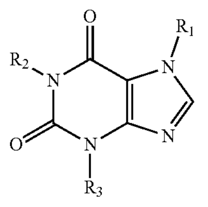

wherein $R_1$, $R_2$, and $R_3$ are independently selected from H and $CH_3$, for improving storage stability of aqueous compositions comprising hydrogen peroxide.

The eighth object of the present invention is a kit-of-parts comprising the composition as defined above and one more composition selected from:

an aqueous composition having a pH in the range of 7 to 12 and comprising one or more oxidative dye precursors and/or oxidative dye couplers, a bleach powder composition comprising one or more persalt(s) and/or peroxy salt(s) and one or more alkalizing agent(s), an aqueous lightening composition comprising one or more alkalizing agent(s) and having a pH in the range of 7 to 12, an aqueous composition having a pH in the range of 7 to 12 comprising one or more reducing agent(s) and one or more alkalizing agent(s).

DETAILED DESCRIPTION OF THE INVENTION

Despite the attempts of the prior art, no satisfactory solution could be delivered to improve chemical and physical storage stability of aqueous oxidizing compositions comprising hydrogen peroxide.

Inventors of the present invention have unexpectedly found out that xanthine and its derivatives increase chemical and physical storage stability of aqueous oxidizing compositions comprising hydrogen peroxide at room and elevated temperature alike. Moreover, xanthine and its derivatives enable the maintenance of active hydrogen peroxide over storage and prevent viscosity changes. Thus, bleaching/lightening, oxidative dyeing, and permanent waving processes were unexpectedly found to be more consistent in performance over time.

Aqueous Oxidizing Composition

The aqueous oxidizing composition according to the invention has a pH in the range of 1 to 6 and comprises:

a) hydrogen peroxide at a concentration of more than 5% by weight, calculated to the total weight of the composition, and b) one or more xanthine and/or xanthine derivative according to the following structure:

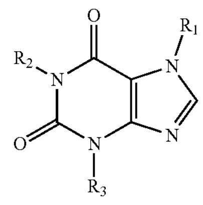

wherein $R_1$, $R_2$, and $R_3$ are independently selected from H and $CH_3$, and/or their mixtures.

It is preferred from the viewpoint of storage stability and safety of the composition that the pH of the composition is 1.25 or more, more preferably 1.5 or more, further more preferably 2 or more.

It is preferred from the viewpoint of storage stability of the composition that the pH of the composition is 5 or less, more preferably 4 or less, further more preferably 3 or less.

For attaining the above-mentioned effects, it is preferred that the pH of the composition is in the range of 1.25 to 5, more preferably in the range of 1.5 to 4, further more preferably in the range of 2 to 3.

It is further preferred from the viewpoint of product performance that the concentration of the compound according to a) is in the range of more than 5% by weight or more, more preferably 6% by weight or more, further more preferably 9% by weight or more, calculated to the total weight of the composition.

It is further preferred from the viewpoint of product performance and user safety that the concentration of the compound according to a) is 20% by weight or less, more preferably 15% by weight or less, further more preferably 12% by weight or less, calculated to the total weight of the composition.

For attaining the above-mentioned effects, it is preferred that the concentration of the compound according to a) is in the range of more than 5% to 20% by weight, more preferably 6% to 15% by weight, further more preferably 9% to 12% by weight, calculated to the total weight of the composition.

Suitable xanthine and/or xanthine derivatives according to the structure of compound b) are Xanthine with $R_1$=$R_2$=$R_3$=H, Theobromine with $R_1$=$R_3$=$CH_3$ and $R_2$=H, Theophylline with $R_2$=$R_3$=$CH_3$ and $R_1$=H, and Caffeine with $R_1$=$R_2$=$R_3$=$CH_3$.

Mixtures of the above are suitable as well.

It is preferred from economic viewpoint that at least one compound according to b) is caffeine.

It is further preferred from the viewpoint of stabilizing performance that the total concentration of compounds according to b) is 0.001% by weight or more, more preferably 0.01% by weight or more, further more preferably 0.02% by weight or more, still more preferably 0.03% by weight or more, calculated to the total weight of the composition.

It is further preferred from the viewpoint of economic reasons as well as stabilizing performance that the total concentration of compounds according to b) is 0.5% by weight or less, more preferably 0.25% by weight or less, further more preferably 0.1 by weight or less, still more preferably 0.08% by weight or less, calculated to the total weight of the composition.

For attaining the above-mentioned effects it is preferred that the total concentration of compounds according to b) is in the range of 0.001% to 0.5% by weight, preferably in the range of 0.01% to 0.25% by weight, more preferably in the range of 0.02% to 0.1% by weight, still more preferably in the range of 0.03% to 0.08% by weight, calculated to the total weight of the composition.

It is preferred from the viewpoint of stabilization performance that the weight ratio of compounds a) to b) is 2 or more, more preferably 20 or more, further more preferably 37.5 or more, further more preferably 100 or more.

It is preferred from the viewpoint of stabilization performance that the weight ratio of compounds a) to b) is 1,000 or less, more preferably 600 or less, further more preferably 400 or less, further more preferably 150 or less.

For achieving the above-mentioned effects, it is preferred that the weight ratio of compounds a) to b) is in the range of 2 to 1,000, more preferably in the range of 20 to 600, further more preferably in the range of 37.5 to 400, further more preferably in the range of 100 to 150.

Form of Aqueous Oxidizing Composition

The composition of the present invention preferably is an emulsion, thickened gel, or a combination thereof, from the viewpoint of cosmetic safety as well as user friendliness.

Lipophilic Compounds as Compounds According to c)

In case the composition of the present invention is formulated as an emulsion and/or thickened emulsion, it is preferred that the composition comprises one or more lipophilic compound(s) as compound(s) according to c).

Preferably, compounds according to c) are selected from $C_{12}$ to $C_{22}$ fatty alcohols, esters of $C_3$ to $C_{22}$ alcohols with $C_{12}$ to $C_{22}$ fatty acids, $C_8$ to $C_{22}$ fatty acids, vegetable oils, and/or silicones, and/or hydrocarbon-based products, and/or their mixtures, from the viewpoint of cosmetic compatibility.

Suitable $C_{12}$ to $C_{22}$ fatty alcohols are are myristyl alcohol, cetyl alcohol, stearyl alcohol, behenyl alcohol, and cetearyl alcohol.

Suitable esters of $C_3$ to $C_{22}$ alcohols with $C_{12}$ to $C_{22}$ fatty acids are isopropyl myristate, isopropyl palmitate, and myristyl myristate.

Suitable $C_8$ to $C_{22}$ fatty acids are oleic acid, linoleic acid, and palmitic acid. Suitable vegetable oils are olive oil, almond oil, sunflower oil, and argan oil. Suitable silicones are non-aminated and/or aminated silicones. The latter are commonly known as amodimethicones.

It is preferred from the viewpoint of forming a stable composition and user friendliness that the total concentration of compounds according to c) is 1% by weight or more, more preferably 2% by weight or more, further more preferably 3% by weight or more, calculated to the total weight of the composition.

It is preferred from the viewpoint of forming a stable composition that the total concentration of compounds according to c) is 20% by weight or less, more preferably 15% by weight or less, further more preferably 12% by weight or less, calculated to the total weight of the composition.

For attaining the above-mentioned effects, the total concentration of compounds according to c) is in the range of 1% to 20% by weight, preferably in the range of 2% to 15% by weight, more preferably in the range of 3% to 12% by weight, calculated to the total weight of the composition.

Surfactants as Compounds According to d)

The composition of the present invention may further comprise one or more surfactant(s) as compound according to d), preferably selected from non-ionic surfactants, anionic surfactants, cationic surfactants, and/or amphoteric/zwitterionic surfactants, and/or their mixtures, more preferably selected from anionic surfactants, from the viewpoint of stabilizing the composition and improving wettability and mixability.

Preferably, the anionic surfactants may be selected from ethoxylated or non-ethoxylated alkyl ether sulfate surfactants, alkyl sulfates, ethoxylated and/or non-ethoxylated alkyl carboxylates, ethoxylated or non-ethoxylated amino acid surfactants, and/or their mixtures, and/or their salts.

Suitable examples are alkyl sulfate or preferably ethoxylated alkyl ether sulfate surfactants or mixtures thereof, and/or salts thereof, having an alkyl chain length of $C_{10}$ to $C_{22}$ and an ethoxylation degree from 1 to 50.

Suitable non-ionic surfactants may be selected from alkyl polyglycosides, ethoxylated triglycerides, ethoxylated fatty alcohols, ethoxylated fatty acid esters, and/or their mixtures.

Suitable cationic surfactants are quaternary ammonium surfactants having a carbon chain length in the range of $C_{12}$ to $C_{22}$ or surfactants having a tertiary amine group and at least one alkyl chain having a carbon chain length in the range of $C_{12}$ to $C_{22}$ such as alkylamidoalkylamine surfactants, and/or their salts. Suitable examples are cetrimonium chloride and behentrimonium chloride.

Suitable amphoteric/zwitterionic surfactants are of betaine type. Suitable compounds may be selected from alkyl betaines and/or alkylamido betaines. A preferred compound selected from alkyl betaines is lauryl betaine. A preferred compound selected from alkylamido betaines is cocamidopropyl betaine. The disclosure also relates to the salts of the compounds.

Suitable concentration ranges for surfactants are in the range of 0.1% to 10% by weight, calculated to the total weight of the composition, from the viewpoint of enhancing wettability of keratin fibers, physical stability, and mixability with other compositions.

Thickening Polymers

From the viewpoint of cosmetic safety, it is further preferred that the composition of the present invention comprises one or more thickening polymer.

The composition of the present invention comprises one or more thickening polymer(s) selected from non-ionic thickening polymers and/or anionic thickening polymers, and/or their mixtures.

Preferably, the thickening polymers are selected from polymers resulting in an aqueous solution and/or aqueous dispersion at pH between 1 and 6 having a viscosity of at least 1,000 mPa·s measured at a polymer concentration of 1% by weight in water at 25° C., calculated to the total weight of the composition, determined by a Brookfield viscometer, such as at 10 rpm for 1 min, with an appropriate spindle at 25° C.

Suitable non-ionic thickening polymers are cellulose-based polymers. Suitable examples of cellulose-based polymers are methylcellulose, hydroxymethylcellulose, hydroxyethylcellulose, hydroxypropylcellulose, hydroxyethyl-methylcellulose, and alkylated hydroxyl celluloses such as $(C_2-C_8)$-alkylcelluloses or cetyl hydroxyethylcellulose.

Suitable anionic thickening polymers are selected from naturally-based anionic polymers and/or synthetic anionic polymers.

Suitably, the natural anionic polymer(s) may be selected from xanthan gum, dehydroxanthan gum, hydroxypropylxanthan gum, carboxymethyl cellulose and starch based polymers such as vegetable starch and/or their synthetically modified derivatives such as hydroxypropyl starch phosphate. Equally suitable are alginic acids, sodium alginates, ammonium alginates, calcium alginates, gum arabic, and guar gum.

Suitable synthetic anionic polymers are associative thickening polymers, such as acrylates/steareth-30 methacrylate copolymer.

The preferred thickening polymer for the composition of the present invention are natural anionic polymers, more preferably xanthan gum and/or dehydroxanthan gum, from the viewpoint of their biodegradability and low environmental impact.

Preferably, the total concentration of thickening polymers of the present invention are 0.1% by weight or more, more preferably 0.25% by weight or more, more preferably 0.5% by weight or more, calculated to the total weight of the composition, from the viewpoint of providing sufficient viscosity to the composition.

Preferably, the total concentration of thickening polymers of the present invention are 15% by weight or less, more preferably 12% by weight or more, further more preferably 10% by weight or less, calculated to the total weight of the composition, from the viewpoint of providing sufficient viscosity to the composition and cost of goods.

For attaining the above-mentioned effects, it is preferred that the total concentration of thickening polymers in the composition of the present invention is in the range of 0.1% to 15% by weight, preferably in the range of 0.25% to 12% by weight, more preferably in the range of 0.5% to 10% by weight, calculated to the total weight of the composition.

It is preferred from the viewpoint of cosmetic safety that the composition of the present invention has a viscosity in the range of 1,000 Pas to 25,000 mPas, preferably 2,000 mPas to 20,000 mPas, more preferably in the range of 2,500 mPas to 17,500 mPas, determined by cone plate viscometry at 25° C. under atmospheric conditions. A suitable viscometer is a Brookfield viscometer with spindle #4.

Method and Use of Stabilizing an Oxidative Composition

The present invention is also directed to a method for stabilizing an aqueous oxidizing composition comprising the steps of:

i) providing an aqueous composition comprising hydrogen peroxide at a concentration of more than 5% by weight, calculated to the total of the composition,
ii) dissolving in the composition as defined in step i) one or more compound(s) according to the following structure:

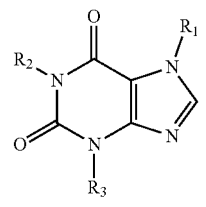

wherein $R_1$, $R_2$, and $R_3$ are independently selected from H and $CH_3$, and/or their mixtures.

The preferred concentration for the composition defined under i) and the preferred compounds and concentrations as defined under ii) are the same as defined for the inventive composition above.

The present invention is also directed to a use of a compound according to the following general structure:

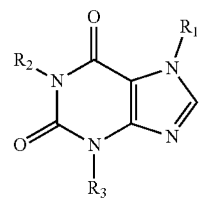

wherein $R_1$, $R_2$, and $R_3$ are independently selected from H and $CH_3$, for improving storage stability of aqueous compositions comprising hydrogen peroxide, preferably for maintaining hydrogen peroxide concentration over storage time.

The preferred concentrations and compounds are the same as defined for the inventive composition above.

Oxidative Dyeing

The present invention is also directed to a method for oxidative dyeing of keratin fibers, preferably human keratin fibers, more preferably human hair, comprising the steps of:

iii) providing the inventive composition as described above,
iv) mixing the composition with an aqueous composition having a pH in the range of 7 to 12 and comprising one or more oxidative dye precursors and/or oxidative dye couplers to prepare a ready-to-use composition having a pH in the range of 7 to 12, v) applying the ready-to-use composition onto keratin fibers and leaving it for a time period of 1 to 60 min, vi) rinsing off the keratin fibers and optionally shampooing the keratin fibers.

Suitable oxidative dye precursors for the composition of step iv) are, for example, p-phenylendiamine and/or its derivatives, p-aminophenol and/or its derivatives, and heterocyclic compounds such as diaminopyrazols and substituted pyrimidines and/or their derivatives and/or their salts.

Furthermore, besides oxidative dye precursors, the composition of step iv) may comprise oxidative dye couplers. Suitable oxidative dye couplers are resorcinol and/or its derivatives, m-aminophenol and/or its derivatives, m-phenylenediamine and/or its derivatives, pyridines and/or its derivatives, and naphthole and/or its derivatives, and/or their salts.

The suitable total concentration of oxidative dye precursors and/or oxidative dye couplers is in the range of 0.001% to 5% by weight, preferably in the range of 0.01% to 4% by weight, more preferably in the range of 0.05% to 3% by weight, still more preferably in the range of 0.1% to 2% by weight, calculated to the total weight of the composition of step iv) before mixing.

Suitably, the composition of step iv) comprises one or more alkalizing agent. Preferably, one or more alkalizing agent(s) is selected from ammonia, alkyl- or alkanolamines according to the general structure

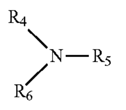

wherein $R_4$, $R_5$, and $R_6$ are same or different H, from $C_1$ to $C_4$ alkyl, $C_3$ to $C_4$ unsaturated alkyl, $C_3$ to $C_4$ branched alkyl, $C_1$ to $C_4$ hydroxyl alkyl, $C_3$ to $C_4$ unsaturated hydroxyl alkyl, $C_3$ to $C_4$ branched hydroxyl alkyl, with the condition that at least one of $R_4$, $R_5$, or $R_6$ is different from H.

It is preferred from the viewpoint of dyeing intensity that the alkalizing agent is selected from ammonia and/or monoethanolamine and/or 2-aminomethyl propanol.

It is further preferred from the viewpoint of sufficient alkalinity and dyeing intensity that the concentration of alkalizing agents in the dyeing composition of step iv) before mixing is in the range of 0.25% to 15% by weight, more preferably in the range of 0.5% to 12.5% by weight, still more preferably in the range of 0.75% to 10% by weight, and still more preferably in the range of 1% to 7.5% by weight, calculated to the total weight of the dyeing composition of step iv) before mixing.

The dyeing composition of step iv) before mixing has a pH in the range of 7 to 12. It is preferred from the viewpoint of buffering capacity that the pH of the dyeing composition of step iv) before mixing is in the range of 7.5 to 11, more preferably in the range of 8.0 to 10, still more preferably in the range of 8.5 to 9.5.

The dyeing composition of step iv) is then mixed with the inventive composition of the present invention of step iii) to form a ready-to-use composition. Suitable mixing ratios by weight are 5:1 to 1:5 (composition of step iv:inventive composition of step iii). Customarily, suitable mixing ratios are 1:1, 1:2, and 1:3 by weight (composition of step iv:inventive composition of step iii).

Suitably, the pH of the ready-to-use composition is in the range of 7 to 12. It is preferred from the viewpoint of accelerated dyeing speed that the pH of the ready-to-use composition is in the range of 7.5 to 11, more preferably 8.0 to 10.5.

The ready-to-use composition is then applied to keratin fibers and left for a time period of 1 min to 60 min as defined in step v). Preferred time ranges for step v) are 5 min to 45 min, more preferred ranges are 10 min to 35 min, from the viewpoint of sufficiently developing the oxidative hair color.

During the application time of the ready-to-use mixture, heat may be applied to the keratin fibers, preferably in a temperature range from 30° C. to 50° C., from the viewpoint of accelerating dyeing speed and cosmetic safety.

After that, the ready-to-use composition is rinsed-off from keratin fibers in step vi) and optionally they are shampooed and optionally blow-dried.

Bleaching and/or Lightening

The present invention is also directed to a method for bleaching and/or lightening of keratin fibers, preferably human keratin fibers, more preferably human hair comprising the steps of:

vii) providing the inventive composition as defined above, viii) mixing the composition with a bleach powder composition comprising one or more persalt(s) and/or peroxy salt(s) and one or more alkalizing agent(s) to prepare a ready-to-use composition having a pH in the range of 7 to 12, ix) applying the ready-to-use composition onto keratin fibers and leaving it for a time period in the range of 1 to 60 min, x) rinsing off the keratin fibers and optionally shampooing the keratin fibers.

The bleach powder composition of step viii) comprises one or more persalt(s) and/or peroxy salt(s). Suitable persalts and/or peroxy salts are sodium persulfate, potassium persulfate, ammonium persulfate, earth alkali peroxides such as magnesium peroxide, melamine peroxide or urea peroxide or phthalimidoperoxy hexanoic acid. The preferred persalts from the viewpoint of bleaching power are sodium, potassium and ammonium persulfate.

It is preferred from the viewpoint of bleaching power and cosmetic safety that the total concentration of persalts and/or peroxy salts in the bleach powder composition of step viii) before mixing is in the range of 10% to 80% by weight, preferably in the range of 15% to 70% by weight, more preferably in the range of 20% to 60% by weight, and still more preferably in the range of 25% to 60% by weight, calculated to the total weight of the bleach powder composition of step viii) before mixing.

The bleach powder composition of step viii) further comprises one or more alkalizing agent(s). Suitable alkalizing agent(s) are metasilicates, in particular sodium metasilicate. It is preferred from the viewpoint of alkalinity that the concentration of metasilicates in the bleach powder composition of step viii) before mixing is in the range of 1% to 20% by weight, more preferably 5% to 15% by weight, calculated to the total weight of the bleach powder composition of step viii) before mixing.

Other suitable alkalizing agent(s) are carbonate and bicarbonate alkali salts such as sodium, potassium, and ammonium salts. The preferred salts are bicarbonate salts and especially preferred is ammonium bicarbonate, from the viewpoint of buffer capacity. Suitable concentration of carbonates in the bleach powder composition of step viii) is in the range of 0.25% to 10% by weight, preferably in the range of 0.5% to 7.5% by weight, more preferably in the range of 0.75% to 5% by weight, and still more preferably in the range of 1% to 4% by weight, calculated to the total weight of the bleach powder composition before mixing, from the viewpoint of buffer capacity and low hair damage.

The bleach powder composition of step viii) is then mixed with the inventive composition of the present invention according to step vii) to form a ready-to-use composition. Suitable mixing ratios by weight are 5:1 to 1:5 (composition of step viii:inventive composition according to step vii). Customarily, suitable mixing ratios are 1:1, 1:2, and 1:3 by weight (composition of step viii:inventive composition according to step vii).

Suitably, the pH of the ready-to-use composition is in the range of 7 to 12. It is preferred from the viewpoint of accelerated dyeing that the pH of the ready-to-use composition is in the range of 7.5 to 11, more preferably 8.0 to 10.5.

The ready-to-use composition is then applied to keratin fibers and left for a time period of 1 min to 60 min as defined in step ix). Preferred time ranges for step ix) are 5 min to 45 min, more preferred ranges are 10 min to 35 min, from the viewpoint of sufficiently developing the oxidative hair color.

Optionally, heat may be applied while leaving the ready-to-use composition onto keratin fibers. Suitable temperature ranges are 30° C. to 50° C.

After that, the ready-to-use composition is rinsed-off from keratin fibers according to step x) and optionally they are shampooed and optionally blow-dried.

The present invention is also directed to a method for bleaching and/or lightening of keratin fibers, preferably human keratin fibers, more preferably human hair comprising the steps of:

xi) providing the inventive composition as defined above,
xii) mixing the composition with an aqueous lightening composition comprising one or more one or more alkalizing agent(s) to prepare a ready-to-use composition having a pH in the range of 7 to 12,
xiii) applying the ready-to-use composition onto keratin fibers and leaving it for a time period in the range of 1 to 60 min,
xiv) rinsing off the keratin fibers and optionally shampooing the keratin fibers.

The aqueous lightening composition of step xii) before mixing preferably is an emulsion comprising one or more lipophilic compound, as also disclosed for the inventive composition.

The aqueous lightening composition preferably has a pH in the range of 8 to 11, more preferably in the range of 8.5 to 10.5, from the viewpoint of lightening performance.

Suitable mixing ratios are similar to the ones disclosed for the bleaching process above while using an aqueous composition instead of a bleaching powder.

Permanent Shaping

The present invention is also directed to a method for permanently shaping keratin fibers, preferably human keratin fibers, more preferably human hair, comprising the steps of:

xv) optionally shampooing the keratin fibers,
xvi) putting hair under mechanical tension,
xvii) applying to keratin fibers an aqueous composition having a pH in the range of 3 to 12 comprising one or more reducing agent(s) and one or more alkalizing agent(s), and leaving the composition for a time period in the range of 1 min to 60 min,
xviii) optionally rinsing off the composition,
xix) providing a composition as defined above, applying it to keratin fibers and leaving it for a time period in the range of 1 min to 30 min,
xx) releasing mechanical tension from keratin fibers,
xxi) rinsing off the keratin fibers and optionally shampooing the keratin fibers, with the provision that steps xvi) and xvii) as well as steps xix) and xx) may be performed in any order. The other steps may be performed exactly in this order as listed above.

The term "permanent shaping" is to be understood as referring to permanent curling and permanent straightening.

Thus, mechanical tension as defined in step xvii) is, for example, provided by putting the keratin fibers on curlers or by straightening the fibers by comb and brush.

The composition as defined in step xvii) comprises one or more reducing agent(s). In principle, any inorganic or organic reducing agent and/or their mixtures are suitable for the purpose of the present invention.

Suitable inorganic reducing agents are sulfite and/or hydrogen sulfite salts such as sodium, potassium, and ammonium salts. Suitable organic reducing agents are thioglycolic acid and/or its salts, cysteamine and/or its salts, thioglycerin and/or its salts, glycerin esters of thioglycolic acid and/or its salts, thiolactic acid and/or its salts, cysteine or its derivatives and/or its salts, and/or their mixtures. Preferred are thioglycolic acid and/or its salts, thiolactic acid and/or its salts, cysteine or its derivatives and/or its salts and sodium, potassium, ammonium sulfites and their mixtures, form the viewpoint of cosmetic safety. The most preferred reducing agents are thioglycolic acid and/or its salts and sodium, potassium, ammonium sulfites, and/or their mixtures, form the viewpoint of cosmetic safety.

It is preferred that the total concentration of reducing agents in the composition of step xvii) is in the range of 0.5% to 20% by weight, more preferably 1% to 15% by weight, still more preferably 2% to 12% by weight, and still more preferably 3% to 10% by weight, calculated to the total weight of the composition of step xvii).

The pH of the composition may be acidic or alkaline and is in the range of 3 to 12, preferably 4 to 11, and most preferably it is alkaline and in the range of 7.5 to 10.5, from the viewpoint of reducing power. The pH may be adjusted with the known organic and/or inorganic acids and alkalizing agents (see above for dyeing and bleaching).

The composition of step xvii) is left on the hair for a period of 1 to 60 min, preferably for a time period of 2 min to 45 min, more preferably for a time period of 5 min to 30 min, and further more preferably for a time period of 5 min to 20 min at ambient temperature. Optionally heat may be applied.

The inventive composition is then applied to hair in step xix) and left for a time period of 1 min to 30 min. It is preferred from the viewpoint of hair damage and oxidation performance that the composition is left on keratin fibers for 2 min to 25 min, more preferably for 3 min to 20 min, and further more preferably for 5 min to 15 min, optionally while applying heat and/or under use of heating device.

Kit-of-Parts

The present invention is also directed to a kit-of-parts comprising the inventive composition as defined above and one more composition selected from:

an aqueous composition having a pH in the range of 7 to 12 and comprising one or more oxidative dye precursors and/or oxidative dye couplers, a bleach powder composition comprising one or more persalt(s) and/or peroxy salt(s) and one or more alkalizing agent(s), an aqueous lightening composition comprising one or more alkalizing agent(s) and having a pH in the range of 7 to 12, an aqueous composition having a pH in the range of 3 to 12 comprising one or more reducing agent(s) and one or more alkalizing agent(s).

It is preferred from the viewpoint of customer friendliness that the aforementioned compositions are separately packed.

It is further preferred that the aqueous composition having a pH in the range of 7 to 12 and comprising one or more oxidative dye precursors and/or oxidative dye couplers is the composition of step iv) before mixing.

It is further preferred that the bleach powder composition comprising one or more persalt(s) and/or peroxy salt(s) and one or more alkalizing agent(s) is the composition of step viii) before mixing.

It is further preferred that the aqueous lightening composition comprising one or more alkalizing agent(s) and having a pH in the range of 7 to 12 is aqueous lightening composition of step xii) before mixing.

It is further preferred that the aqueous composition having a pH in the range of 3 to 12 comprising one or more reducing agent(s) and one or more alkalizing agent(s) is the permanent shaping composition of step xvii).

The following examples are to illustrate the invention, but not to limit it.

EXAMPLES

Example 1

The following compositions were prepared by dissolving caffeine as compound according to b) in an aqueous composition of hydrogen peroxide under constant stirring:

| Ingredient | Inventive composition 1 [% by weight] | Comparative composition 1 [% by weight] |
|---|---|---|
| Caffeine | 0.03 | — |
| Hydrogen peroxide | 9.3 | |
| Phosphoric acid | q.s. ad pH 2.5 | |
| Water | Ad 100.0 | |

The compositions were prepared and stored under controlled conditions at 40° C. for 12 months. Hydrogen peroxide content was analyzed by titration and the following concentrations were measured:

| Time [months] | Inventive composition 1 [% by weight] | Comparative composition 1 [% by weight] |
|---|---|---|
| 0 | 9.3 | 9.3 |
| 1 | 9.0 | 8.9 |
| 3 | 8.7 | 7.4 |
| 6 | 8.7 | 6.4 |
| 12 | 8.6 | 6.3 |

As a result, the compound according to b) could maintain 92% of hydrogen peroxide activity over 1 year, whereas the comparative composition without compound according to b) was only 68% active after 1 year.

Methods

Hydrogen peroxide concentration was measured by iodometric titration using a Mettler Toledo DL58 titrator equipped with a Redox electrode and a 0.1 N sodium-thiosulfate-solution.

Example 2

The following compositions were prepared by dissolving theobromine as compound according to b) in an aqueous composition of hydrogen peroxide under constant stirring:

| Ingredient | Inventive composition 2 [% by weight] | Comparative composition 2 [% by weight] |
|---|---|---|
| Theobromine | 0.03 | — |
| Hydrogen peroxide | 6.0 | |
| Phosphoric acid | q.s. ad pH 2.0 | |
| Water | Ad 100.0 | |

The same methods as in example 1 were used in the analysis below.

| Time [days] | Inventive composition 2 [% by weight] | Comparative composition 2 [% by weight] |
|---|---|---|
| 0 | 5.9 | 5.9 |
| 1 | 5.9 | 5.8 |
| 5 | 5.9 | 4.6 |
| 8 | 5.9 | 4.4 |
| 12 | 5.9 | 4.2 |
| 20 | 5.8 | 3.3 |

Example 3

| | % by weight |
|---|---|
| Caffeine | 0.01 |
| Cetearyl alcohol | 4.0 |
| Sodium lauryl sulfate | 0.8 |
| Phosphoric acid | q.s. ad pH 1.5 |
| Tetrasodium EDTA | 0.05 |
| Hydrogen peroxide | 6.0 |
| Water | ad 100.0 |

The concentration of caffeine as compound according to b) may also be adjusted to 0.05%, 0.1%, or 0.5% or any values in between to achieve the same technical effect.

The concentration of hydrogen peroxide may be adjusted to 9%, 12%, 15%, or 20% by weight, or any value in between.

Example 4

| | % by weight |
|---|---|
| Theobromine | 0.01 |
| Cetearyl alcohol | 4.0 |

-continued

| | % by weight |
|---|---|
| Sodium lauryl sulfate | 0.8 |
| Phosphoric acid | q.s. ad pH 2.5 |
| Tetrasodium EDTA | 0.05 |
| Hydrogen peroxide | 6.0 |
| Water | ad 100.0 |

The concentration of theobromine as compound according to b) may also be adjusted to 0.05%, 0.1%, or 0.5% or any values in between to achieve the same technical effect.

Theobromine may also be replaced by xanthin or theophylline.

The concentration of hydrogen peroxide may be adjusted to 9%, 12%, 15%, or 20% by weight, or any value in between.

Example 5

| | % by weight |
|---|---|
| Caffeine | 0.01 |
| Theobromine | 0.05 |
| Theophylline | 0.05 |
| Cetearyl alcohol | 4.0 |
| Sodium lauryl sulfate | 0.8 |
| Phosphoric acid | q.s. ad pH 3.0 |
| Tetrasodium EDTA | 0.05 |
| Hydrogen peroxide | 6.0 |
| Water | ad 100.0 |

The concentration of theobromine as compound according to b) may also be adjusted to 0.05%, 0.1%, or 0.5% or any values in between to achieve the same technical effect.

Theobromine may also be replaced by xanthin or theophylline.

The concentration of hydrogen peroxide may be adjusted to 9%, 12%, 15%, or 20% by weight, or any value in between.

Example 6

The following oxidative dyeing composition was prepared:

| | % by weight |
|---|---|
| Cetearyl alcohol | 12 |
| Sodium cetearyl sulfate | 2 |
| Cocamide MEA | 5 |
| Oleic acid | 2 |
| Tetrasodium EDTA | 1 |
| Sodium sulfite | 1 |
| Ammonium hydroxide | 5 |
| Ammonium chloride | 1 |
| Toluene-2,5-Diamine sulfate | 0.75 |
| Resorcinol | 0.10 |
| 4-Chlorresorcinol | 0.25 |
| m-Aminophenol | 0.05 |
| 4-Amino-2-Hydroxytoluene | 0.05 |
| Fragrance | 0.5 |
| Water | ad 100 |

The above composition had a pH of 9.9.

The oxidative dyeing composition was then mixed with the inventive composition 1 and comparative composition 1 of example 1 stored after 1 year in a weight ratio of 1:1 to yield a ready-to-use composition. The ready-to-use composition had a pH of around 9.5.

The ready-to-use compositions were applied to human hair and left for 30 min at room temperature. After that, the compositions were rinsed-off with water, the hair was shampooed, and blow-dried.

The hair was found to be intensely red-brown colored with the inventive composition 1, whereas the hair had less color intensity with the comparative composition 1.

Example 7

The following bleaching powder composition was prepared:

| | % by weight |
|---|---|
| Hydroxyethylcellulose | 3 |
| Tetrasodium EDTA | 2 |
| Sodium carbonate | 1 |
| Ammonium persulfate | 11 |
| Potassium persulfate | 36 |
| Sodium metasilicate | 10 |
| Mineral oil | 8 |
| Diatomaceous Earth | to 100 |

The bleaching powder composition from above was then mixed with the inventive composition 1 and comparative composition 1 of example 1 stored after 1 year at a weight ratio of 1:2 (bleaching powder:inventive composition 1) to yield a ready-to-use composition having a pH around 9.8.

The ready-to-use compositions were then applied onto human hair and left for 30 min at room temperature. After that, the compositions were rinsed-off with water, the hair was shampooed, and blow-dried.

The hair was found to be intensely bleached with inventive composition 1, whereas the degree of lightening was visually lower for the hair streak bleached with comparative composition 1.

Example 8

The following permanent shaping composition was prepared:

| | % by weight |
|---|---|
| Ammonium thioglycolate (60%) | 21.3 |
| Ammonium hydrogen carbonate | 5.0 |
| 1,3-butylene gylcol | 3.0 |
| Amodimethicone | 0.2 |
| PEG-40-Hydrogenated castor oil | 0.7 |
| Fragrance | 0.4 |
| Ammonia (25% active) | ad pH 8.3 |
| Water | ad 100.0 |

Human hair was shampooed and the hair was put under mechanical tension on curlers. Then the composition from above was applied to hair and left for 15 min at 40° C. The composition was then rinsed-off with water.

Then the inventive composition 1 and comparative composition 1 of example 1 stored after 1 year and was applied to hair and left for 15 min at room temperature. Tension from hair was then released and the curlers were removed. The hair was then rinsed-off, shampooed, and blow-dried.

The hair was found to be intensely curled and had good cosmetic feeling with the inventive composition 1, whereas the streak treated with the comparative composition 1 had poor hair feel and less curling intensity.

The invention claimed is:

1. An aqueous oxidizing composition having a pH in the range of 1 to 6, comprising:

a) hydrogen peroxide at a concentration of more than 5% by weight, calculated to the total weight of the composition;

b) one or more compounds according to the following structure:

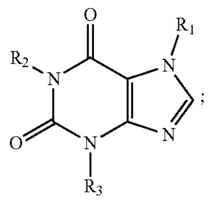

and (c) one or more lipophilic compounds;

where $R_1$, $R_2$, and $R_3$ are independently selected from H and $CH_3$, and/or their mixtures, wherein a total concentration of the compounds according to b) is in the range of 0.001% to 0.08% by weight, calculated based on a total weight of the composition, the viscosity of the composition is in the range of 1,000 mPas to 25,000 mPas, determined by cone plate viscometry at 25° C. under atmospheric conditions, and the weight ratio of component a) to component b) is from 20 to 400.

2. The composition according to claim 1, wherein the concentration of hydrogen peroxide is in the range of more than 5% to 20% by weight, calculated to the total weight of the composition.

3. The composition according to claim 1, wherein at least one of the compounds according to b) is caffeine.

4. The composition according to claim 1, wherein the compound c) is at least one selected from the group consisting of a $C_{12}$ to $C_{22}$ fatty alcohol, an esters of a $C_3$ to $C_{22}$ alcohol with a $C_{12}$ to $C_{22}$ fatty acid, a $C_8$ to $C_{22}$ fatty acid, a vegetable oil, a silicone, a hydrocarbon-based product, and a mixture thereof.

5. The composition according to claim 1, wherein the total concentration of the compound c) is in the range of 1% to 20% by weight, calculated to the total weight of the composition.

6. The composition according to claim 1, further comprising one or more surfactants as compound d).

7. The composition according to claim 6, wherein the compound d) is at least one selected from the group consisting of a non-ionic surfactant, an anionic surfactant, a cationic surfactant, an amphoteric/zwitterionic surfactants, and a mixture thereof.

8. A method for oxidative dyeing of keratin fibers, the method comprising:

iii) providing a composition as defined in claim 1, iv) mixing the composition with an aqueous composition having a pH in the range of 7 to 12 and comprising one or more oxidative dye precursor(s) and/or one or more oxidative dye coupler(s) to prepare a ready-to-use composition having a pH in the range of 7 to 12, v) applying the ready-to-use composition onto keratin fibers and leaving the applied ready-to-use composition for a time period of 1 to 60 min, vi) rinsing off the keratin fibers and optionally shampooing the keratin fibers.

9. A method for bleaching and/or lightening of keratin fibers comprising the steps of:

vii) providing an aqueous oxidizing composition as defined in claim 1, viii) mixing the composition with a bleach powder composition comprising one or more persalts and/or peroxy salts and one or more alkalizing agents to prepare a ready-to-use composition having a pH in the range of 7 to 12, ix) applying the ready-to-use composition onto keratin fibers and leaving the applied ready-to-use composition for a time period in the range of 1 to 60 min, and x) rinsing off the keratin fibers and optionally shampooing the keratin fibers.

10. A method for permanently shaping keratin fibers, comprising the steps of:

xv) optionally shampooing the keratin fibers, xvi) putting keratin fibers under mechanical tension, xvii) applying to keratin fibers an aqueous composition having a pH in the range of 3 to 12 and comprising one or more reducing agents and one or more alkalizing agents, and leaving the composition for a time period in the range of 1 min to 60 min, xviii) optionally rinsing off the composition, xix) applying an aqueous oxidizing composition as defined in claim 1 to the keratin fibers and leaving the applied composition for a time period in the range of 1 min to 30 min, xx) releasing mechanical tension from the keratin fibers, and xxi) rinsing off the keratin fibers and optionally shampooing the keratin fibers, with the provision that steps xvi) and xvii) as well as steps xx) and xxi) may be performed in any order.

* * * * *